United States Patent [19]
Kichefski et al.

[11] Patent Number: 5,342,340
[45] Date of Patent: Aug. 30, 1994

[54] REUSABLE DIAPER

[75] Inventors: Conrad M. Kichefski; Mary B. Madryga, both of Minneapolis; Kurt R. Madryga, Burnsville; Christopher G. Struble, Deephaven; Kathleen A. Madryga, Burnsville, all of Minn.

[73] Assignee: New World Diaper Service, Minneapolis, Minn.

[21] Appl. No.: 967,223

[22] Filed: Oct. 27, 1992

[51] Int. Cl.$^5$ .................. A61F 13/15; A61F 13/20
[52] U.S. Cl. .................. 604/385.1; 604/358; 604/386; 604/393; 604/394; 604/398; 604/399
[58] Field of Search ............ 604/385.2, 386–387, 604/391–394, 397–399

[56] References Cited

U.S. PATENT DOCUMENTS

| | | | |
|---|---|---|---|
| 2,606,558 | 8/1952 | Kennette | 604/399 |
| 3,349,769 | 10/1967 | Piekarski | 604/370 |
| 3,369,545 | 2/1968 | Wanberg | 604/366 |
| 3,520,303 | 7/1970 | Endres | 604/370 |
| 4,486,192 | 12/1984 | Sigl | 604/366 |
| 4,578,073 | 3/1986 | Dysart et al. | 604/385.2 |
| 4,627,847 | 12/1986 | Puletti et al. | 604/366 |
| 4,978,345 | 12/1990 | Holliday et al. | 604/378 |
| 5,108,385 | 4/1992 | Snyder | 604/397 |
| 5,188,626 | 2/1993 | Toyoda et al. | 604/358 |
| 5,263,948 | 11/1993 | Karami et al. | 604/385.1 |

*Primary Examiner*—Randall L. Green
*Assistant Examiner*—P. Zuttarelli
*Attorney, Agent, or Firm*—Patterson & Keough

[57] ABSTRACT

A reusable leakproof diaper which is as convenient in use as a disposable diaper and includes a one-or-more layered absorbent rectangular liner attached by strips of liquid impervious material to a liquid impervious outer shell. A closure system, such as snap fasteners, single looped closures, buttons, or hooks is mounted on the outer shell. The sides of the outer shell include elastic strips along the portion of the shell that forms a leg opening when the diaper is in use. The unique design for attaching the inner absorbent liner to the liquid impervious outer shell provides the diaper with improved resistance to leakage.

10 Claims, 1 Drawing Sheet

REUSABLE DIAPER

TECHNICAL FIELD OF THE INVENTION

The present invention relates to the field of diapers. In particular, it relates to a reusable diaper made of an absorbent cloth inner layer and an integral liquid impervious outer layer that is particularly designed to reduce leakage.

BACKGROUND OF THE INVENTION

Over the past several decades the diaper market has shifted from substantially cloth multi-piece reusable diapers to one piece plastic and paper single use disposable diapers. The shift to single use disposable diapers has occurred primarily because of the convenience, fit, sanitation, and absorbency they offer. Disposable diapers, however, have a significant negative impact on the environment because a) they are the fastest growing substance in landfills b) they remain intact and do not decompose for several hundred years and c) they pose a significant risk of contamination to our nation's ground water.

While several reusable diapers have been recently introduced in the market place to compete with single use disposable diapers, a convenient, leakproof, sanitary, fitted, one piece reusable diaper is not yet available. Reusable diapers have been described in detail in, for example, U.S. Pat. No. 5,032,119 (Hookano) issued Jul. 16, 1991, and U.S. Pat. No. 5,069,672 (Wippler et al.) issued Dec. 3, 1991. The Hookano patent describes an all-cotton I-shaped diaper with elastic material around the leg openings of the diaper. Though this design improves on the traditional rectangular single layer cotton diaper, the problems of diaper leaking remains. The Wippler patent discloses a reusable, generally rectangular diaper comprising absorbent inner and outer layers with a liquid impervious layer between the inner and outer layers and a removable absorbent insert placed in opposed pockets carried by the inner layer of the diaper. Disadvantages of the Wippler diaper include chafing of a baby's skin caused by the edges of the insert pockets and dislodging of the removable insert as the baby moves.

The main objective of the present invention is to provide a reusable cloth diaper that has the convenience, leakproofness, absorbency, sanitation, and fit of a disposable diaper.

A further objective of the present invention is to provide a reusable cloth diaper that has the convenience, leakproofness, absorbency, sanitation, and fit of a disposable diaper yet retains the advantage of efficient washing and drying along with the environmental neutrality of cloth diapers.

SUMMARY OF THE INVENTION

A diaper disclosed in accordance with the present invention provides environmental advantages over disposable diapers and functional and laundering advantages over previous reusable diapers. The leakproof diaper hereof is comprised of a one-or-more layered absorbent cloth substantially rectangular inner liner carrying an underfacing strip at each end of the inner liner. The underfacing strip attaches the opposed ends of the inner liner to an hour-glass shaped liquid impervious outer shell. The underfacing is formed of a liquid impervious material whereby the underfacing provides a barrier between the absorbent inner liner and the edges of the outer shell to minimizing leakage. The outer shell is edged with a liquid impervious outer binding and elastic edging ensuring a snug and leakproof fit for the diaper. A fastening system is mounted on the outer shell allowing for easy removal of the soiled diaper from a child. The front top edge of the outer shell has a flap facing that extends above the waistband when the diaper is fastened that prevents leakage along the top, front margin of the diaper.

The inner cloth layer is attached to the outer liquid impervious layer only at the lengthwise ends thereof to form an integral, one piece unit that nevertheless has excellent air circulation characteristics to improve drying time of the diaper during the cleaning cycle.

DETAILED DESCRIPTION OF THE INVENTION

Figure 1:
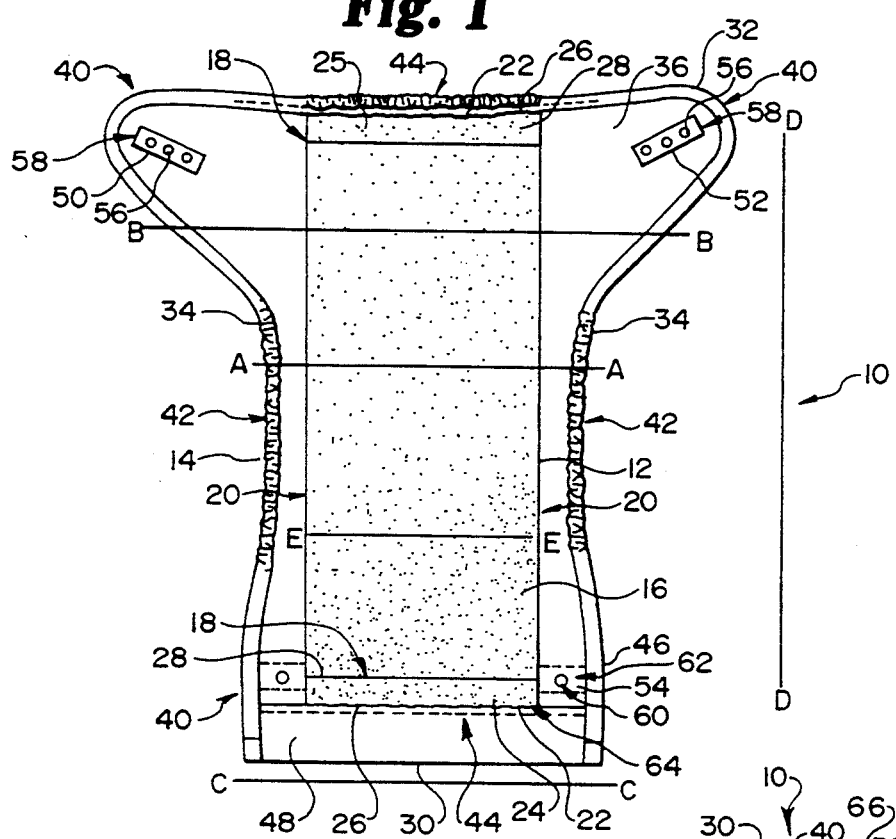
FIG. 1 is a top plan view of a reusable diaper in accordance with the invention.

Referring to the drawings, a diaper 10 in accordance with the present invention includes a substantially rectangular inner liner 12 and an hourglass-shaped outer shell 14.

The inner liner 12 is comprised of one-or-more layers of absorbent material 16. Each layer 16 carries opposed ends 18 and opposed side edges 20. An underfacing 22 extends beyond the opposed ends 18 of the inner liner 12. In the preferred embodiment, three layers 16 of absorbent material are sewn together along the side edges 20.

The underfacing 22 comprises underfacing strips 24, 25 of a liquid impervious material. Each underfacing strip 24, 25 may include a double layer of material and presents an outer margin 26 and an inner margin 28. The underfacing strips 24, 25 permanently attach the inner liner 12 to the outer shell 14 along each end 18 of the inner liner 12 by means of a sewn seam, or any other suitable attachment means.

The outer shell 14 is made of a liquid impervious material formed in a generally hourglass shape. The outer shell 14 presents a front edge 30, back edge 32, opposed side margins 34, an inner face 36 and an outer face 38. The outer shell 14 of the diaper 10 broadly includes a fastening system 40, leg elastic 42, waist elastic 44, binding 46 and front facing 48.

The fastening system 40 includes a left back fastener 50, a right back fastener 52 and a front coupling strip 54. The back fasteners 50, 52 each include a plurality of female snap connectors 56 attached to a ribbon of fabric 58. Each back fastener 50, 52 is fixedly mounted on the inner face 36 of the outer shell 14 in the area defined by the intersection of the back edge 32 and each side margin 34.

Figure 2:
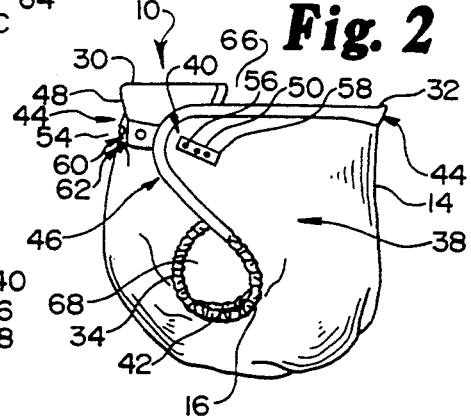
FIG. 2 is a perspective view of the diaper depicted in a closed configuration.
Figure 3:
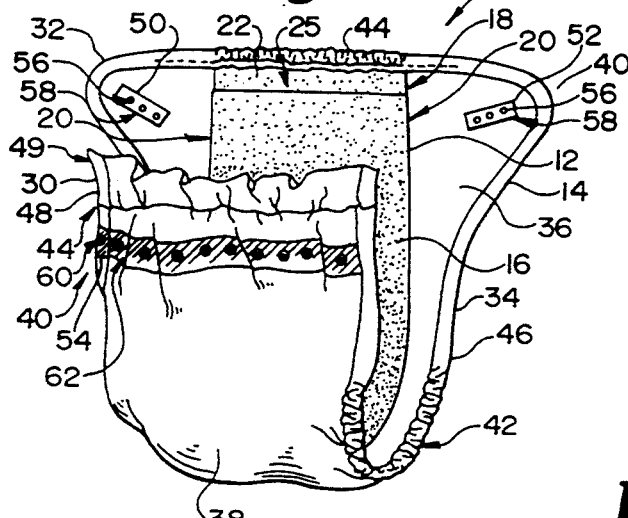
FIG. 3 is a perspective view of the diaper depicted in an open configuration.
Figure 4:
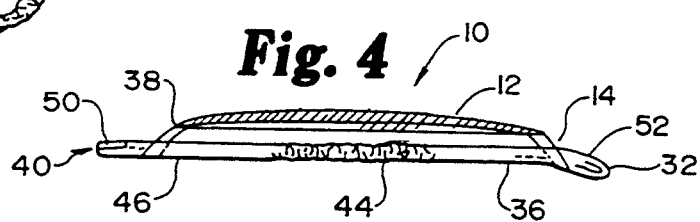
FIG. 4 is a side elevational view of the diaper in accordance with the present invention.

The front coupling strip 54 includes a plurality of male snap connectors 60 attached to a front ribbon of fabric 62. The front ribbon 62 is sewn to the outer face 38 of the outer shell 14 parallel to and below the front edge 30 such that, as shown in FIGS. 2 and 3, the female and male snap connectors 56, 60 can be joined to form the diaper 10. Though the preferred embodiment of the fastening system describes female and male snap connectors, the fastening system could also be made of hook and pile elements, buttons and buttonholes or hook and eye assemblies.

The leg elastic 42 and waist elastic 44 of the outer shell 14 preferably are formed of the same material as elastic strips commonly associated with underwear or like apparel. The leg elastic 42 is attached to the outer shell 14 along portions of the side margins 34. The waist elastic 44 is attached to the outer shell 14 along portions of the front edge 30 and back edge 32.

The binding 46 is made of a thin strip of liquid impervious material and attached along the front edge 30, back edge 32 and side margins 34 of the outer shell 14. In the preferred embodiment, the binding 46 is made of the same material as the outer shell 14 and encases the leg elastic 42 and waist elastic 44.

In an alternate embodiment as depicted in FIG. 3, the waist elastic 44 is attached to the outer shell 14 along the front facing 48 whereby the outer shell 14 and front facing 48 are gathered into ruffle 49.

The front facing 48 is preferably a double layer of liquid impervious material carried along the front edge 30 of the outer shell 14 and presents a liner edge 64. The facing 48 is formed by folding a piece of liquid impervious material in half and attaching the open end along the liner edge 64.

As best shown in FIG. 1, the inner liner 12 is attached to the inner face 36 of the outer shell 14 along the back edge 32 of the outer shell 14 by underfacing strip 25 and along the liner edge 64 of the facing 48 of the outer shell 14 by underfacing strip 24.

In the preferred embodiment, the proportions of the inner liner 12 and the outer shell 14 are such that the length (annotated A—A in the drawings) of the distance between the opposed side margins 34 of the outer shell 14 is less than the length (annotated B—B in the drawings) of the back edge 32 of the outer shell 14 and is less than the length (annotated C—C in the drawings) of the top edge 30 of the outer shell 14 and the length (C—C) of the top edge 30 of the outer shell 14 is less than the length (B—B) of the back edge 32 of the outer shell 14. The inner liner 12 is generally rectangular in shape with the distance (annotated D—D in the drawings) between the opposed ends 18 of the inner liner 12 greater than the distance (annotated E—E in the drawings) between the opposed side edges 20 whereby the inner liner 12 fits within the space defined by the front edge 30, back edge 32 and opposed side margins 34 of the outer shell 14.

In operation, the diaper 10 is placed on a baby in a manner that is similar to the use of a disposable diaper. The female and male snap connectors 56, 60 of the fastening system 40 are joined around a baby's waist such that the front edge 30 and back edge 32 define a waist opening 66 and the side margins 34 of the outer shell 14 define leg openings 68. By varying which snap connectors are joined, the diaper 10 can be tightened or loosened to adjust to the size of the baby.

The absorbent cloth inner liner 12 retains liquids and cradles solids while the liquid impervious outer shell 14 prevents the liquids from leaking through the outer face 38 of the outer shell 14. The facing 48 extends slightly above the baby's waist to prevent additional leakage as a baby moves and bends. The rectangular shape and position of the inner liner 12 places the absorbent layers 16 of the inner liner 12 closest to the baby without greatly restricting the baby's movement. The hourglass shape of the outer shell 14 maximizes the coverage of the diaper while minimizing the amount of material between the baby's legs unlike a conventional cloth diaper.

The leg elastic 42 keeps the diaper 10 snugly engaged with the baby's legs when the diaper is in place on that baby. The waist elastic 44 keeps the diaper 10 snugly engaged with baby's waist when the diaper is in place on that baby. The binding 46 prevents leakage around leg and waist openings 66, 68 and minimizes skin irritation and chafing from elastic strips.

The underfacing strips 24, 25 isolate the absorbent inner liner 12 from the front edge 30 and back edge 32 of the outer shell 14, such that no part of the inner liner 12 is in proximal, liquid transferring abutment with the edges 30, 32 of the outer shell 14. The liquid retention (leakproofness) of the diaper 10 is greatly improved over previously known diaper designs.

The unitary construction of the diaper 10 enhances its ease of use and streamlines washing by eliminating the need to wash a removable outer plastic protector or a removable inner absorbent insert. In addition, the unique design enhances the durability and lifespan of the diaper through repeated washings and uses.

It is understood that while certain forms of the present invention have been illustrated and described herein, it is not to be limited to the specific forms or arrangements or parts described and shown.

We claim:

1. A reusable undergarment for control of incontinence adapted to be placed around user's waist and legs comprising:
   an inner liner means of absorbent material for absorbing liquid, said inner liner means presenting a front margin and a rear margin;
   an outer shell comprised of liquid impervious material, said outer shell presenting a front edge and a back edge; and
   front and rear liquid impervious underfacing extending generally along and substantially coextensive with the width of said inner liner front margin and said inner liner rear margin respectively for operably, fixedly securing the inner liner means to the outer shell inboard of the front and back edges thereof whereby said inner liner means is operably coupled to and maintained in liquid transfer isolation from, said front edge and said back edge of said outer shell.

2. The invention as claimed in claim 1, said underfacing means comprising front and rear strips of liquid impervious material.

3. The invention as claimed in claim 2, said inner liner presenting opposed side margins extending between said front and rear margins, said inner liner being coupled to said outer shell only along said inner liner front and rear margins.

4. The invention as claimed in claim 3, said inner liner being generally rectangular in shape and presenting an inner liner periphery defining an inner liner width, said outer shell presenting opposed, contoured side edges extending between said front edge and said back edge to define an irregular outer shell width that includes an outer shell minimum width, said inner liner width being less than said outer shell minimum width such that said inner liner is isolated from said outer shell edges around the entire inner liner periphery.

5. The invention as claimed in claim 4, including fastening means for operably fastening said outer shell back edge to said outer shell front edge around said user's waist to present a diaper waistline, said fastening means including adjustment means for conforming the size of said waistline to the size of said user's waist.

6. The invention as claimed in claim 5 wherein said inner liner means is comprised of a plurality of absorbent layers.

7. The invention as claimed in claim 6, said outer shell side edge presenting a generally hourglass shape whereby said outer shell contoured side edges generally conform to the shape of said user's legs when worn by said user.

8. The invention as claimed in claim 7 including biasing means operably carried along at least a portion of said outer shell side edges for tightly conforming said side edges to said user's legs.

9. A reusable undergarment for control of incontinence adapted to be placed around a user's waist and legs comprising:

an inner liner means of absorbent material for absorbing liquid, said inner liner means being generally rectangular in shape and presenting a front margin, a rear margin, opposed side margins and an inner liner periphery defining an inner liner width, said inner liner means comprising of a plurality of absorbent layers;

outer shell means presenting a front edge, a back edge and opposed, contoured side edges extending between said front edge and said back edge to define an irregular outer shell width that includes an outer shell minimum width, said outer shell minimum width being greater than said inner width such that said inner liner means is isolated from said outer shell side edges around the entire inner liner periphery, each of said outer shell side edges presenting a generally hourglass shape whereby said outer shell side edges generally conform to the shape of said user's legs when worn by said user and include biasing means operably carried along at least a portion of said outer shell side edges for tightly conforming said outer shell side edges to said user's legs, said outer shell including fastening means for operably fastening said outer shell back edge to said outer shell front edge around said user's waist to present a diaper waistline, said fastening means including adjustment means for conforming the size of said waistline to the size of said user's waist, said outer shell means being of liquid impervious material, said outer shell means including liquid impervious facing means operably attached to said outer shell front edge for providing a barrier to liquid transfer between said inner liner means and said outer shell front edge; and liquid impervious underfacing means for permanently attaching said inner liner means in a spaced apart relationship with said outer shell means along at least portions of said front edge and said back edge to form a single unitary piece whereby said inner liner means is attached to and maintained in liquid transfer isolation from said front edge and said back edge of said outer shell, said underfacing means comprising front and rear strips of liquid impervious material operably coupled along said inner liner means front margin and rear margin respectively for operable attachment of said front margin to said outer shell front edge, and said rear margin to said outer shell back edge.

10. The invention as claimed in claim 9, said facing means including gathering means operably attached to said facing means and to said outer shell means for gathering said facing means and said outer shell means to present a ruffle along said outer shell front edge.

* * * * *